United States Patent
Litvak et al.

(10) Patent No.: US 8,401,657 B1
(45) Date of Patent: Mar. 19, 2013

(54) SPECTRAL PROFILE ADJUSTMENT OF INCOMING AUDIO SIGNALS FOR COCHLEAR IMPLANT PATIENTS

(75) Inventors: Leonid M. Litvak, Los Angeles, CA (US); Aniket Saoji, Northridge, CA (US); Abhijit Kulkarni, Newbury Park, CA (US)

(73) Assignee: Advanced Bionics, LLC, Valencia, CA (US)

( * ) Notice: Subject to any disclaimer, the term of this patent is extended or adjusted under 35 U.S.C. 154(b) by 561 days.

(21) Appl. No.: 12/325,984

(22) Filed: Dec. 1, 2008

(51) Int. Cl.
*A61N 1/00* (2006.01)
(52) U.S. Cl. ............... 607/57; 607/55; 607/56
(58) Field of Classification Search ............. 607/55–57; 623/10
See application file for complete search history.

(56) References Cited

U.S. PATENT DOCUMENTS

| | | | |
|---|---|---|---|
| 4,819,647 A | 4/1989 | Byers et al. | |
| 5,601,617 A * | 2/1997 | Loeb et al. | 607/56 |
| 6,218,753 B1 | 4/2001 | Asano et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 7,171,272 B2 * | 1/2007 | Blamey et al. | 607/57 |
| 2005/0107843 A1 * | 5/2005 | McDermott et al. | 607/57 |

* cited by examiner

*Primary Examiner* — Niketa Patel
*Assistant Examiner* — Mallika D Fairchild
(74) *Attorney, Agent, or Firm* — AdvantEdge Law Group, LLC

(57) ABSTRACT

Methods and systems for normalizing a spectral profile corresponding to an audio signal include detecting a spectral profile of an incoming audio signal and comparing the spectral profile of the incoming audio signal to a reference spectral profile. The methods further include using the comparison to determine an adjusted spectral profile that more closely matches the reference spectral profile than does the spectral profile of the incoming audio signal and applying electrical stimulation representative of the adjusted spectral profile to a cochlear implant patient.

21 Claims, 15 Drawing Sheets

SPECTRAL PROFILE ADJUSTMENT OF INCOMING AUDIO SIGNALS FOR COCHLEAR IMPLANT PATIENTS

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels. However, in traditional cochlear implants, extraneous noise in an audio signal may decrease the performance of the cochlear implants in various situations from the perspective of a patient wearing the implant. For example, extraneous environmental noise in an audio signal may make it difficult for a cochlear implant patient to effectively hear speech contained within an audio signal. Additionally, portions of an audio signal, such as a speech portion of an audio signal, may be altered by the patient's environment, resulting in decreased performance of the cochlear implant. For example, in an enclosed space such as a room, a speech signal may include a combination of direct sound as well as sound reflected off the walls and ceiling of the room.

SUMMARY

Methods of adjusting a spectral profile of an incoming audio signal for a cochlear implant patient include detecting a spectral profile of an incoming audio signal and comparing the spectral profile of the incoming audio signal to a reference spectral profile. The methods further include using the comparison to determine an adjusted spectral profile that more closely matches the reference spectral profile than does the spectral profile of the incoming audio signal and applying electrical stimulation representative of the incoming audio signal to a patient in accordance with the adjusted spectral profile.

Systems for adjusting a spectral profile of an incoming audio signal for a cochlear implant patient include a sound processor communicatively coupled to an implantable cochlear stimulator. The sound processor is configured to detect a spectral profile of an incoming audio signal and compare the spectral profile of the incoming audio signal to a reference spectral profile. The sound processor is also configured to use the comparison to determine an adjusted spectral profile that more closely matches the reference spectral profile than does the spectral profile of the incoming audio signal. The implantable cochlear stimulator is configured to apply electrical stimulation representative of the incoming audio signal to a patient in accordance with the adjusted spectral profile.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for adjusting a spectral profile corresponding to an incoming audio signal and applying electrical stimulation representative of the incoming audio signal in accordance with the adjusted spectral profile to a cochlear implant patient are described herein. In some examples, a sound processor is configured to detect a spectral profile of an incoming audio signal and compare the spectral profile of the incoming audio signal to a reference spectral profile. The sound processor may be configured to use the comparison to determine an adjusted spectral profile that more closely matches the reference spectral profile than does the spectral profile of the incoming audio signal. An implantable cochlear stimulator is communicatively coupled to the sound processor and configured to apply electrical stimulation representative of the incoming audio signal to the cochlear implant patient in accordance with the adjusted spectral profile. In this manner, the patient may more effectively recognize the contents of the incoming audio signal.

As used herein, an "incoming audio signal" may include speech, music, or other sounds as may serve a particular application and may include one or more recognizable attributes such as, but not limited to, words, lyrics, notes, musical patterns, harmonic relationships, pitches, and/or noises. In some examples, an incoming audio signal may also include noise.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one example" or "an example" means that a particular feature, structure, or characteristic described in connection with the example is included in at least one example. The appearance of the phrase "in one example" in various places in the specification are not necessarily all referring to the same example.

Figure 1:
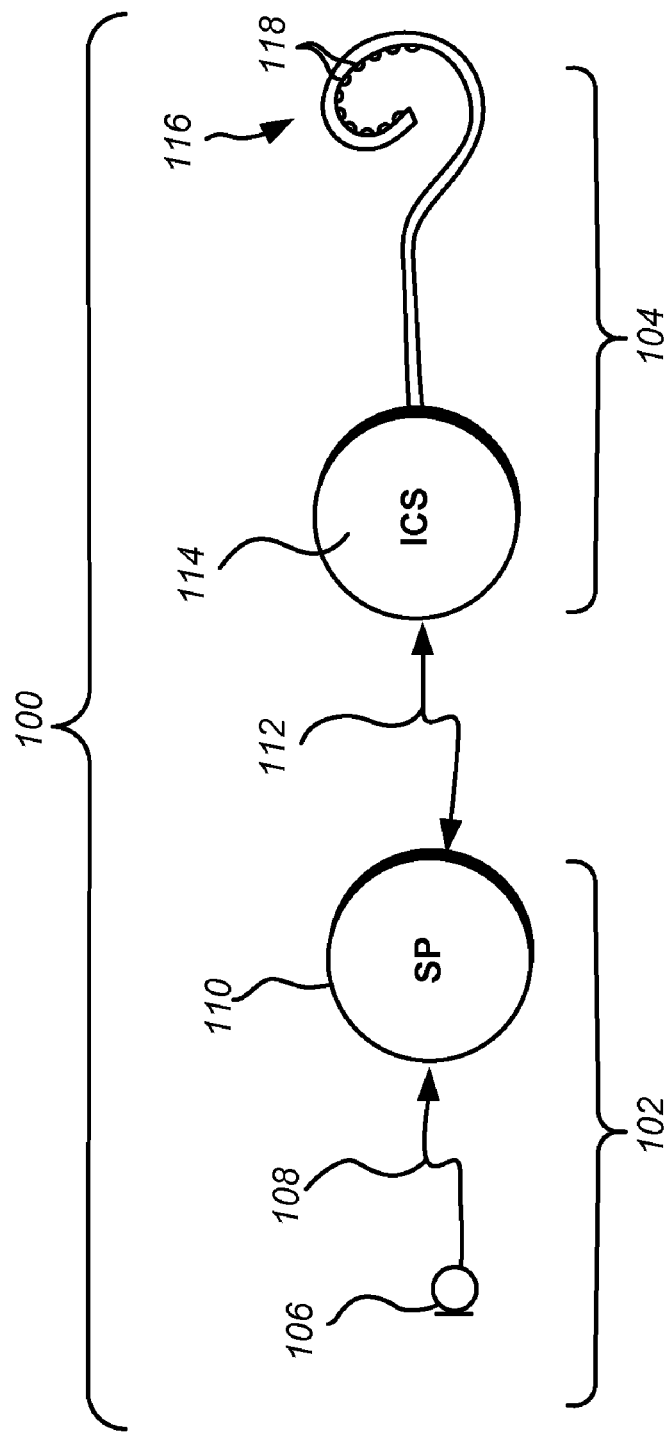
FIG. 1 illustrates an exemplary cochlear implant system according to principles described herein.

FIG. 1 illustrates an exemplary cochlear implant system 100 that may be used in accordance with the present methods and systems. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system 100 of FIG. 1 includes a sound processor portion 102 and a cochlear stimulation portion 104. The sound processor portion 102 may include a sound processor 110, a microphone 106, and/or additional circuitry as best serves a particular application. The cochlear stimulation portion 104 may include an implantable cochlear stimulator 114, a number of electrodes 118 disposed on a lead 116, and/or additional circuitry as best serves a particular application. The components within the sound processor portion 102 and the cochlear stimulation portion 104 will be described in more detail below.

The microphone 106 of FIG. 1 is configured to sense audio signals and convert the sensed signals to corresponding electrical signals. In some examples, the audio signal may include speech. The audio signal may additionally or alternatively include music, noise, and/or other sounds. The electrical signals are sent from the microphone 106 to the sound processor 110 via a communication link 108. Alternatively, the microphone 106 may be connected directly to, or integrated with, the sound processor 110. The sound processor 110 processes these converted audio signals in accordance with a selected sound processing strategy to generate appropriate stimulation parameters for controlling the implantable cochlear stimulator 114. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 114.

The lead 116 shown in FIG. 1 is configured to be inserted within a duct of a cochlea. As shown in FIG. 1, the lead 116 includes a multiplicity of electrodes 118, e.g., sixteen electrodes, spaced along its length. It will be understood, however, that any number of electrodes 118 may be disposed on the lead 116. The lead 116 may be substantially as shown and described in U.S. Pat. No. 4,819,647 or 6,218,753, each of which is incorporated herein by reference in its respective entirety. As will be described in more detail below, electronic circuitry within the implantable cochlear stimulator 114 is configured to generate and apply electrical stimulation to one or more stimulation sites within the cochlea via selected stimulation channels (i.e., pairs or groups of the individual electrodes 118) in accordance with a specified stimulation strategy defined by the sound processor 110.

The implantable cochlear stimulator 114 and the sound processor 110 may be communicatively coupled via a suitable data or communication link 112. It will be understood that the data communication link 112 may include a bi-directional communication link and/or one or more dedicated unidirectional communication links.

In some examples, the sound processor 110 and the microphone 106 comprise an external portion of the cochlear implant system 100 and the implantable cochlear stimulator 114 and the electrode lead 116 comprise an implantable portion of the system 100 that is implanted within a patient's body. In alternative embodiments, one or more portions of the sound processor 110 are included within the implantable portion of the cochlear implant system 100.

The external and implantable portions of the cochlear implant system 100 may each include one or more coils configured to transmit and receive power and/or control signals via the communication link 112. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed audio signal. The external coil may also transmit power from the external portion to the implantable portion of the cochlear implant system 100.

It will be noted that, in some embodiments, both the sound processor 110 and the implantable cochlear stimulator 114 may be implanted within the patient, either in the same housing or in separate housings. If the sound processor 110 and the implantable cochlear stimulator 114 are in the same housing, the communication link 112 may be realized with a direct wire connection within such housing. If the sound processor 110 and the implantable cochlear stimulator 114 are in separate housings, the communication link 112 may include one or more inductive links, for example.

Figure 2:
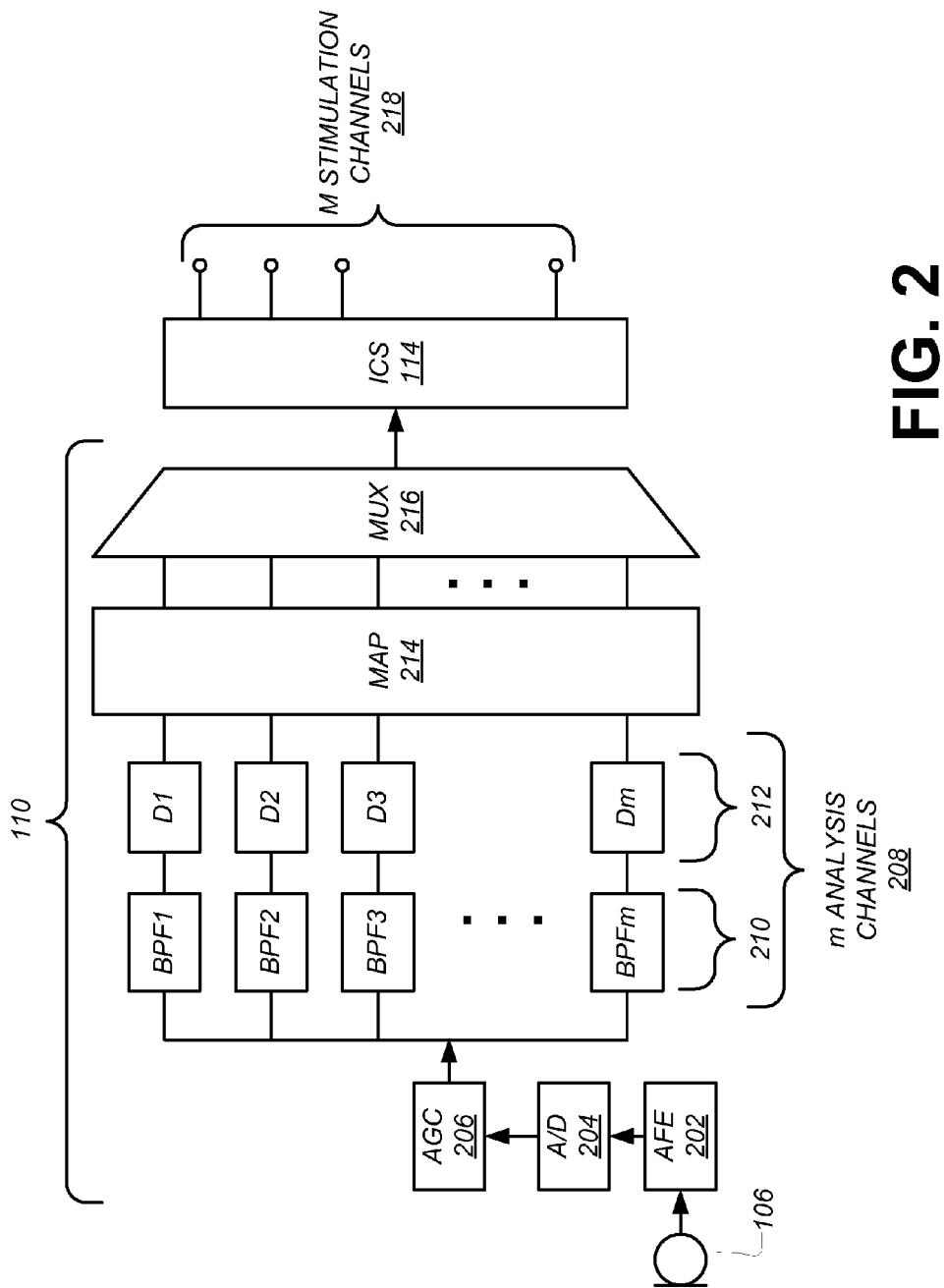
FIG. 2 is a functional block diagram of an exemplary sound processor and implantable cochlear stimulator according to principles described herein.

FIG. 2 is a functional block diagram of an exemplary sound processor 110 and implantable cochlear stimulator 114. The functions shown in FIG. 2 are merely representative of the many different functions that may be performed by the sound processor 110 and/or the implantable cochlear stimulator 114.

As shown in FIG. 2, the microphone 106 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) function 206.

After appropriate automatic gain control, the digital signal is then processed in one of a number of digital signal processing or analysis channels 208. For example, the sound processor 110 may include, but is not limited to, eight analysis channels 208. Each analysis channel 208 may respond to a different frequency band of the sensed audio signal due to a series of band pass filters 210.

As shown in FIG. 2, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include a rectification circuit followed by an integrator circuit.

After energy detection, the signals within each of the m analysis channels 208 are forwarded to a mapping stage 214. The mapping stage 214 is configured to map the signals in each of the m analysis channels 208 to one or more of M stimulation channels 218. In other words, the information contained in the m analysis channels 208 is used to define the electrical stimulation pulses that are applied to the patient by the implantable cochlear stimulator 114 via the M stimulation channels 218. As mentioned previously, pairs or groups of individual electrodes 118 may make up the M stimulation channels 218.

In some examples, the mapped signals are serialized by a multiplexer 216 and transmitted to the implantable cochlear stimulator 114. The implantable cochlear stimulator 114 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue shown in FIG. 3.

Figure 3:
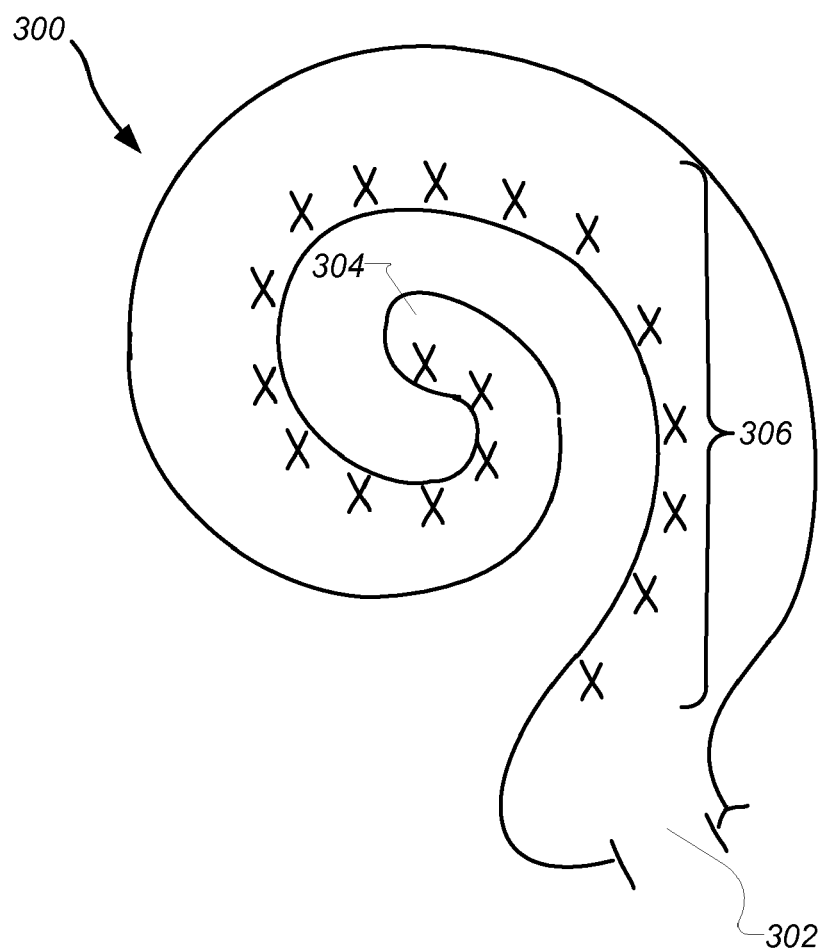
FIG. 3 illustrates a schematic structure of the human cochlea highlighting elements according to principles described herein.

FIG. 3 illustrates a schematic structure of the human cochlea 300. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. A cochlear prosthesis, such as cochlear implant system 100, may therefore be implanted within a patient with sensorineural hearing loss and configured to apply electrical stimulation to different locations within the cochlea 300 to provide the sensation of hearing.

The effectiveness of a cochlear implant system 100 is at least in part dependent on the physiological characteristics of the patient. Hence, a particular set of stimulation parameters may be optimal for one patient and sub-optimal for another. Moreover, the optimal stimulation parameters for a particular patient may vary during the patient's lifetime.

Additionally or alternatively, the effectiveness of a cochlear implant system 100 may be dependent on a listening environment of the patient. For example, a patient may adequately detect speech and/or other sounds in a quiet environment, but have difficulties detecting speech and/or other sounds in a noisy environment. This is because the listening environment of a cochlear implant patient affects the spectral profile of an incoming audio signal. As used herein, a "spectral profile" represents relative spectral levels or intensities of an incoming audio signal measured over an input frequency spectrum. As will be described in more detail below, a cochlear implant patient may have difficulties detecting speech and/or other sounds included within an audio signal having an "abnormal" spectral profile when compared to a reference spectral profile to which the patient is accustomed.

Figure 4:
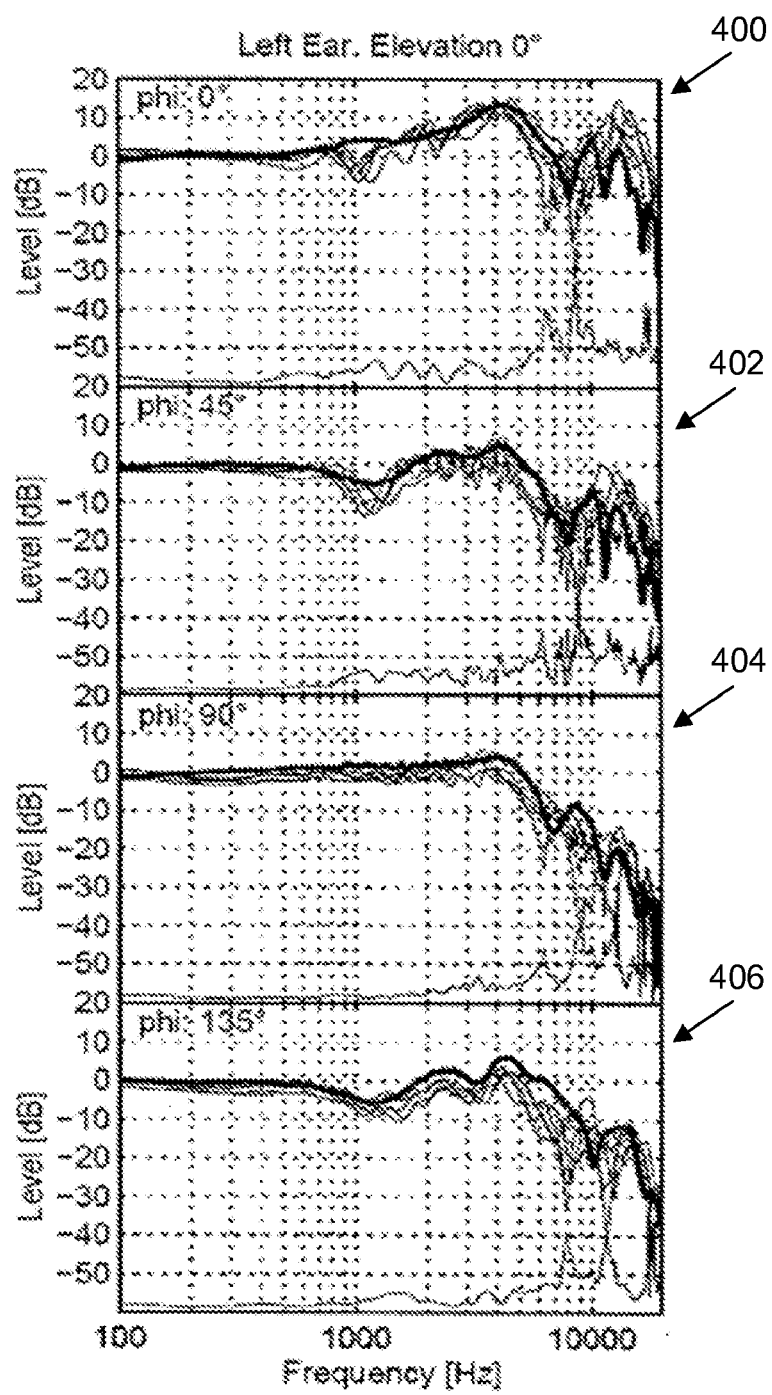
FIG. 4 depicts graphs showing variations in an incoming sound spectrum based on the position of a speaker relative to a cochlear implant patient according to principles described herein.

To illustrate the effect of a listening environment on a spectral profile of an incoming audio signal, FIG. 4 depicts a series of graphs 400 through 406 showing variations in the spectrum of an incoming audio signal based on the position of a speaker relative to a cochlear prosthesis worn by a patient. Each of the graphs 400, 402, 404, and 406 shows a spectrum of incoming sound in an environment in which a speaker is in the proximity of a cochlear implant patient. The incoming sound is detected as an incoming audio signal by a cochlear implant microphone (e.g., microphone 106) located in or near the patient's left ear. Graph 400 shows an incoming sound spectrum as detected by the cochlear implant microphone when a speaker is located at an initial position horizontally and radially outward relative to the patient's left ear (azimuth is 0° relative to the patient). The graphs 402, 404, and 406 each show an incoming sound spectrum as detected by the cochlear implant microphone when the same speaker is located at horizontally clockwise positions relative to the position of the speaker in graph 400 (azimuths of the graphs 402, 404, and 406 are 45°, 90°, and 135° respectively relative to the patient). As illustrated in the graphs 400 through 406, an incoming sound spectrum may change significantly based on a position of a speaker relative to a cochlear implant microphone worn by a patient.

Figure 5A:
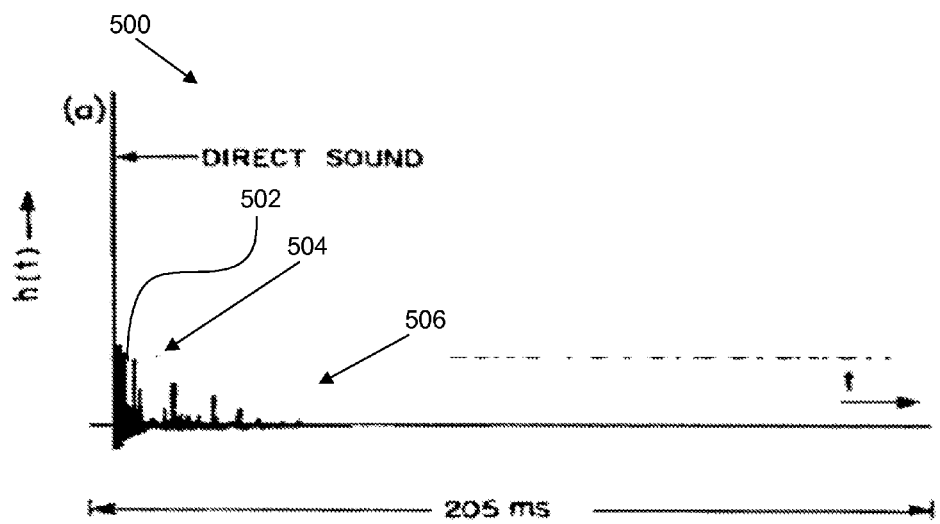
FIG. 5A depicts a graph showing sound reflections and reverberations in an enclosed listening environment according to principles described herein.
Figure 5B:
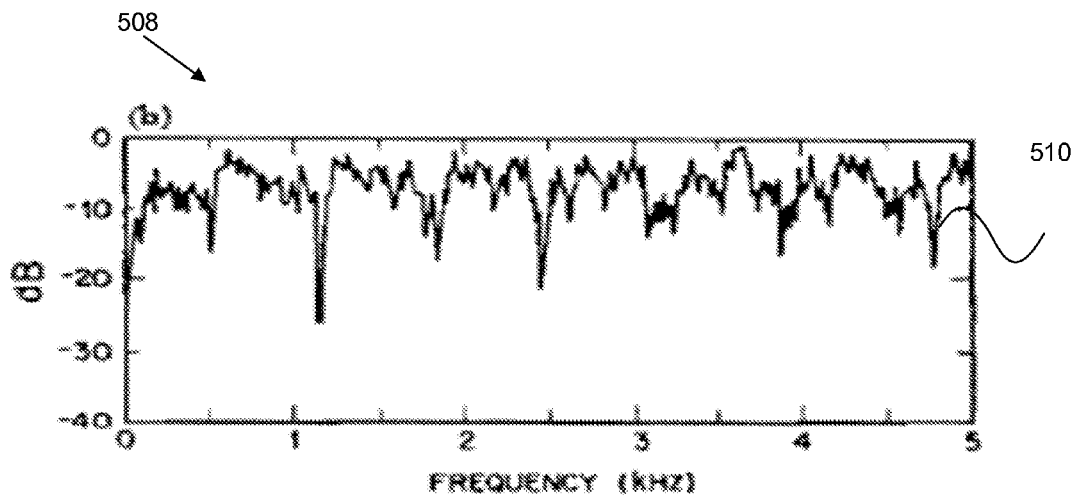
FIG. 5B depicts a graph showing a spectrogram of sound in an enclosed environment according to principles described herein.

To further illustrate the effect of a listening environment on a spectral profile of an incoming audio signal, FIGS. 5A and 5B depict graphs showing sound reflections and reverberations in a enclosed listening environment, such as a room or other listening environment that is at least partially enclosed, and their effect on a spectrogram of the sound in the listening environment. As shown in the graph 500 of FIG. 5A, sounds in an enclosed listening environment may be reflected and reverberated within the listening environment. For example, sound in a room may be reflected off walls of the room. Line 502 in the graph 500 represents sound that is reflected and reverberated in an enclosed listening environment over a period of time. A sound, such as a sound produced by a speaker in the enclosed listening environment, will initially result in early reflections 504 followed by late reverberations 506 as the sound is reflected and reverberated off of surfaces in the listening environment.

The early reflections 504 may result in notches in a spectrogram of the sound. For example, FIG. 5B shows a graph 508 that includes a spectrogram of a sound measured in an enclosed environment. A spectral profile of the sound is represented by line 510. As shown in FIG. 5B, the line 510 includes a plurality of notches resulting from the early reflections 504 as the sound is reflected off of surfaces in the enclosed listening environment. Additionally, the late reverberations 506 may at least partially distort a spectral profile of the sound. For example, the late reverberations 506 may increase lower-frequency portions of the sound. Accordingly, reflections and reverberations may distort a spectral profile of an audio signal received by a cochlear implant patient, as illustrated in graph 508.

Additional environmental factors may also affect a spectral profile of an incoming audio signal. For example, speech signals produced by different speakers may have varying spectral profiles.

As will be described in more detail below, the systems and methods described herein facilitate adjustment of a spectral profile corresponding to an incoming audio signal so that a cochlear implant patient may more effectively recognize or perceive the contents of the audio signal. To this end, a reference spectral profile may be computed based on the spectral profiles of one or more incoming audio signals. If the spectral profile of a particular incoming audio signal differs from the reference spectral profile by more than a predefined amount, an adjusted spectral profile that more closely matches the reference spectral profile may be generated. Electrical stimulation representative of the incoming audio signal may then be applied to the patient in accordance with the adjusted spectral profile.

Figure 6A:
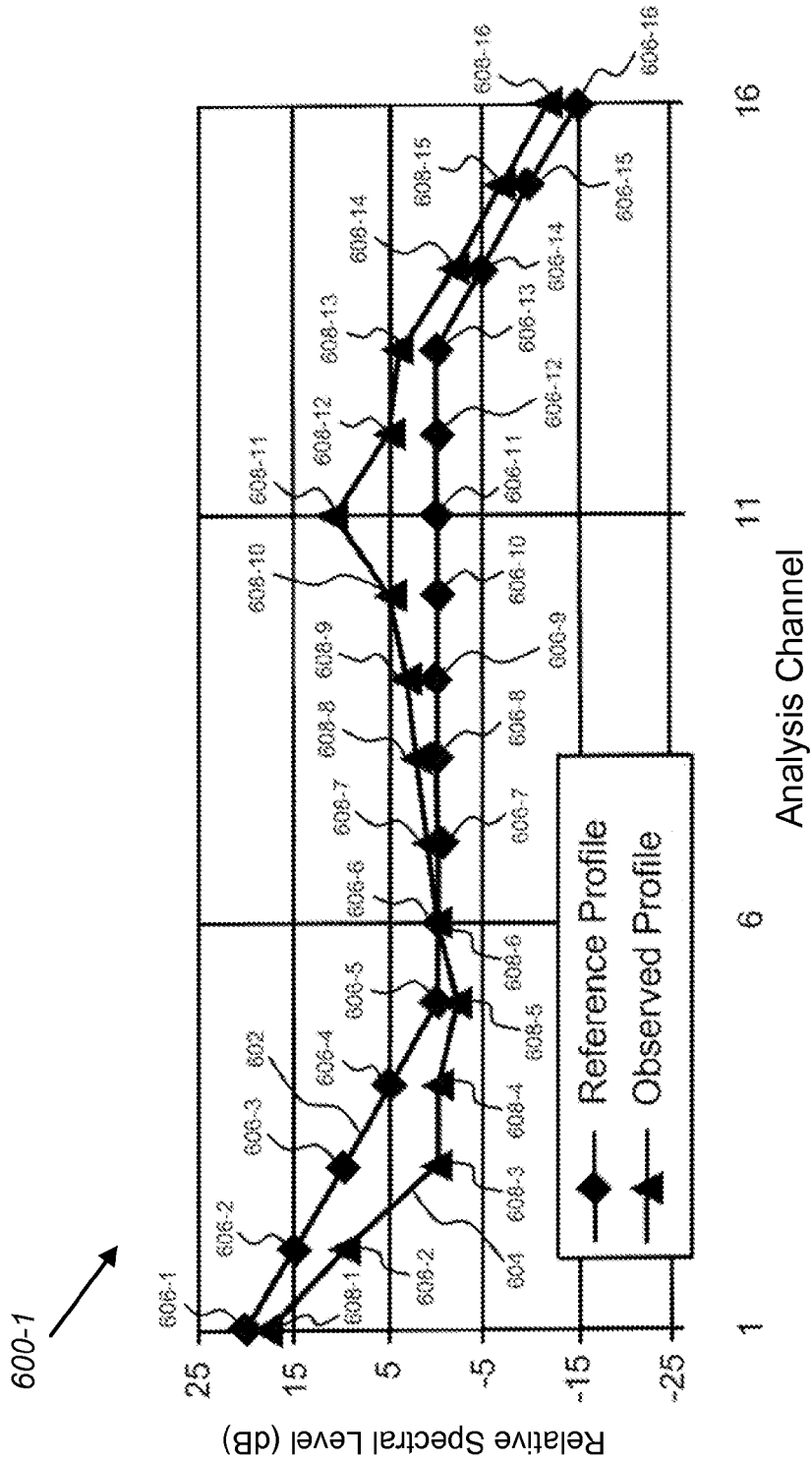
FIGS. 6A-6B depict graphs showing exemplary spectral profiles across a spectrum of analysis channels according to principles described herein.

FIG. 6A depicts a graph 600-1 showing a reference spectral profile 602 and a spectral profile 604 corresponding to an incoming audio signal (referred to herein as an "observed spectral profile 604"). As shown in the graph 600-1 in FIG. 6A, a number of dots 606-1 through 606-16 (collectively referred to herein as "dots 606") are superimposed on a line representing the reference spectral profile 602. Additionally, a number of dots 608-1 through 608-16 (collectively referred to herein as "dots 608") are superimposed on a line representing the observed spectral profile 604. Each of the dots 606 and 608 may represent a relative spectral level (in decibels) measured at a particular analysis channel 208. It will be recognized in the examples given herein that each analysis channel 208 corresponds to a distinct frequency or range of frequencies. It will also be recognized that each analysis channel 208 may correspond to a particular stimulation channel 218 located within a cochlea.

In some examples, the reference spectral profile 602 may represent an average spectral profile of one or more incoming audio signals. To this end, the sound processor 110 may be configured to detect a spectral profile of each of the incoming audio signals and process the detected spectral profiles in order to determine an average spectral profile. The incoming audio signals used to determine the average spectral profile may be measured during one or more discrete time intervals. Alternatively, the sound processor 110 may be configured to dynamically compute the average spectral profile as each incoming audio signal is received by the sound processor 110. While distinct audio signals are referred to herein as being used to generate the average spectral profile, it will be recognized that these distinct audio signals may each correspond to a distinct time segment of a single continuous audio signal.

In some examples, the sound processor 110 may be configured to selectively include only spectral profiles corresponding to audio signals measured in relatively low-noise environments in the computation of the average spectral profile. In this manner, incoming audio signals containing a relatively high noise level will not skew the average spectral profile.

Alternatively, the sound processor 110 may be configured to filter or otherwise separate noise from an incoming audio signal prior to including the audio signal in the computation of the average spectral profile. For example, an incoming audio signal may include a noise component and a speech component. The sound processor 110 may be configured to filter or separate the noise component from the speech component. In this manner, only the speech component may be used to compute the average spectral profile. The noise component may be identified and separated from the speech component using any suitable algorithm or process as may serve a particular application.

In yet another alternative example, the sound processor 110 may be configured to measure a signal-to-noise ratio of an incoming audio signal and include the incoming audio signal in the average spectral profile computation only if the signal-to-noise ratio is above a predetermined threshold. The signal-to-noise ratio may be measured in any suitable manner as may serve a particular application.

The one or more incoming audio signals used to determine the reference spectral profile 602 may be processed at a time and/or in an environment determined by a cochlear implant patient or other user. For example, a user may manually initiate measurement of spectral profiles corresponding to incoming audio signals used to determine the reference spectral profile 602. Alternatively, the sound processor 110 may be configured to automatically measure spectral profiles of audio signals used to determine reference spectral profile 602 at particular times, intervals, and/or under specified environmental sound conditions. For example, the sound processor 110 may include a detection module (see, e.g., detection module 1202 in FIG. 12) configured to detect a listening environment of the patient. The sound processor 110 may be configured to measure the spectral profiles of one or more incoming audio signals only when an environment has an overall incoming audio signal-to-noise ratio that is above a specified threshold value. Additionally, the sound processor 110 may be configured to measure one or more incoming audio signals when a specified condition is satisfied, such as, for example, when a specified time has elapsed and/or when a spectral profile of a speech portion of an incoming audio signal differs to a specified degree from a pre-existing reference spectral profile 602.

The sound processor 110 may also be configured such that it does not update the reference spectral profile 602 under various environmental conditions. For example, the sound processor 110 may include a detection module capable of identifying specified environmental conditions under which a user may not wish to update the reference spectral profile 602, such as environmental conditions where a significant portion of an incoming audio signal includes music. A user may also manually adjust the sound processor 110 so that it does not update the reference spectral profile 602 under various conditions, such as when the user is listening to music.

In some alternative examples, the reference spectral profile 602 may be generated by a device external to the cochlear implant system 100. For example, a pre-determined reference spectral profile 602 may be generated and transferred from an external device to the sound processor 110 where it may be stored by the sound processor 110 to be used in processing incoming audio signals.

In yet other alternative examples, the reference spectral profile 602 may be derived based on a patient's performance in a speech recognition test. For example, a speech recognition test may be performed each time an audio signal is applied to the patient with a new spectral profile. The speech recognition test may be configured to determine a number of words contained within the audio signal that are correctly identified by the patient. By dividing the number of words correctly identified by the total number of words contained within the audio signal, a recognition score measured in percent correct may be obtained. A spectral profile corresponding to the highest recognition score may be selected as the reference spectral profile 602.

The observed spectral profile 604 shown in FIG. 6A may represent a measured spectral profile of an incoming audio signal. The observed spectral profile 604 may be measured in one of various environments, such as in an environment containing extraneous environmental noise and/or in an environment in which the audio signal may include a combination of direct sound as well as sound reflected off walls of an enclosed space. In some examples, the incoming audio signal corresponding to the observed spectral profile 604 may include a relatively high amount of noise, such as extraneous environmental noise and/or altered speech, at least in comparison to the audio signals corresponding to the reference spectral profile 602. In at least one example, the observed spectral profile 604 may represent a spectral profile of an audio signal obtained in an environment in which a cochlear implant patient may have a relatively difficult time distinguishing and/or clearly understanding speech or other desirable sound portions of the audio signal without appropriate adjustment to one or more stimulation parameters in the cochlear implant system 100.

In some examples, the reference spectral profile 602 may be determined by averaging a plurality of observed spectral profiles (such as observed spectral profile 604) from audio signals measured over a specified period of time. For example, the reference spectral profile 602 may represent an average of observed spectral profiles of audio signals measured over a period of at least 10 seconds. In environments containing a relatively high amount of noise, the reference spectral profile 602 may be determined by averaging only observed spectral profiles from incoming audio signals measured during time periods in which the incoming audio signals have a relatively large signal-to-noise ratio.

In some instances, the observed spectral profile 604 may differ from the reference spectral profile 602. As shown in FIG. 6A, the observed spectral profile 604 may differ from the reference spectral profile 602 by different amounts at different analysis channels 208. For example, the difference in relative spectral level between dot 608-3 on the observed spectral profile 604 and dot 606-3 on the reference spectral profile 602 may be greater than the difference in relative spectral level between dot 608-2 on the observed spectral profile 604 and dot 606-2 on the reference spectral profile 602. Additionally, the relative spectral level of the observed spectral profile 604 may be higher or lower than the relative spectral level of the reference spectral profile 602 at different analysis channels 208. For example, as illustrated in FIG. 6A, the relative spectral level of the observed spectral profile 604 may be lower than the relative spectral level of the reference spectral profile 602 at channels 1 through 5 and the relative spectral level of the observed spectral profile 604 may be higher than the relative spectral level of the reference spectral profile 602 at channels 7 through 16. It will be recognized that the reference spectral profile 602 and the observed spectral profile 604 shown in FIG. 6A are merely illustrative and that they may have any alternative shape or characteristic as may serve a particular application.

In some examples, the sound processor 110 may be configured to compare the observed spectral profile 604 to the reference spectral profile 602 by measuring one or more differences between the reference spectral profile 602 and the observed spectral profile 604, such as differences between spectral levels within each of the analysis channels 208. The sound processor 110 may then use the comparison between the reference spectral profile 602 and the observed spectral profile 604 to determine an adjusted spectral profile that may be used as a basis for applying electrical stimulation representative of the incoming audio signal to the cochlear implant patient.

Figure 6B:
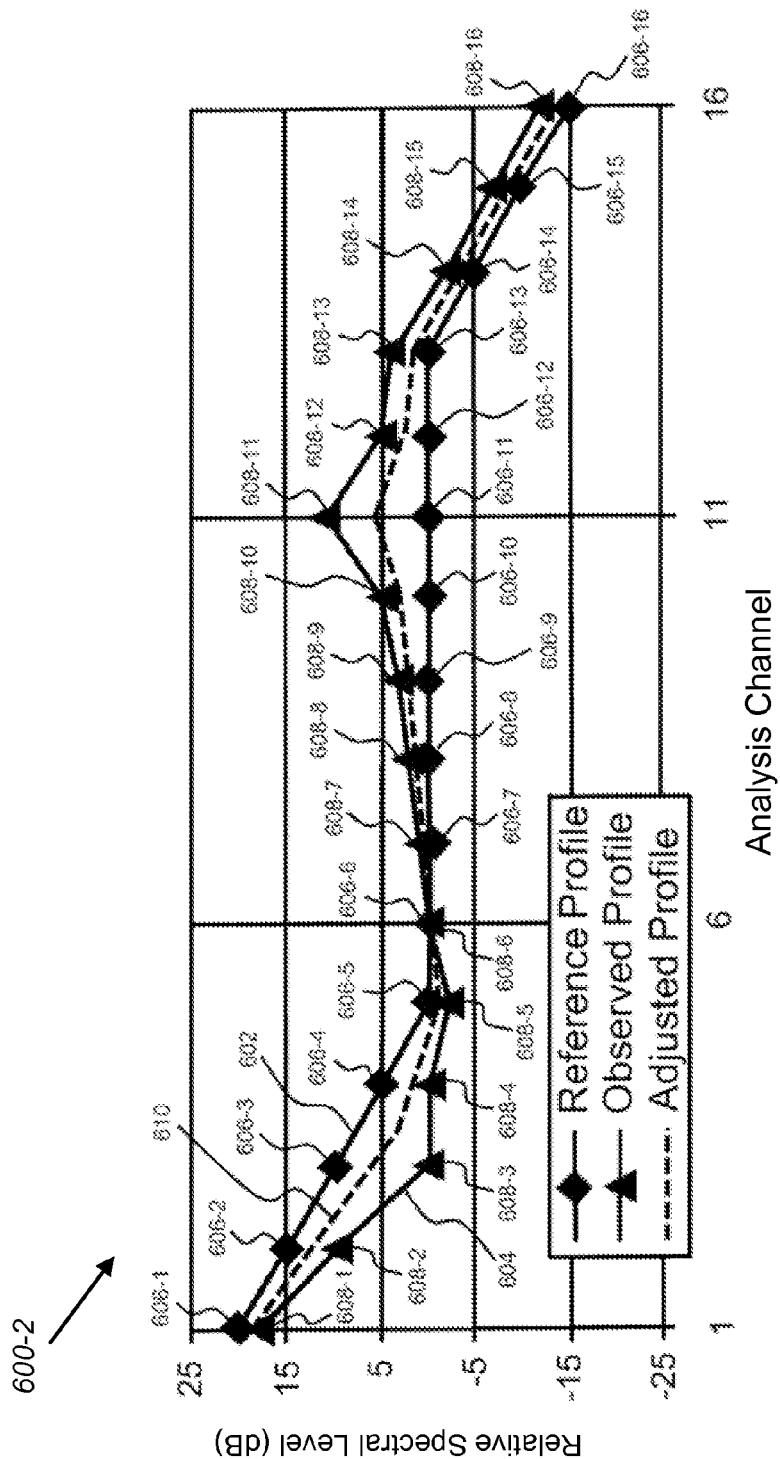

To illustrate, FIG. 6B depicts a graph 600-2 including an adjusted spectral profile 610. As shown in FIG. 6B, the adjusted spectral profile 610 may more closely match the reference spectral profile 602 than does the observed spectral profile 604. In other words, the differences between one or more spectral levels of the adjusted spectral profile 610 and the reference spectral profile 602 are smaller than corresponding differences between one or more spectral levels of the observed spectral profile 604 and the reference spectral profile 602. In certain examples, the adjusted spectral profile 610 may substantially match the observed spectral profile 604.

In some examples, prior to calculating the adjusted spectral profile 610, the reference spectral profile 602 may be determined by dividing spectral profiles of incoming audio signals by the absolute (or overall) level of the incoming audio signals. Likewise, the observed spectral profile 604 may be determined by dividing a spectral profile of an incoming audio signal by the absolute level of the incoming audio signal. Accordingly, the reference spectral profile 602 and the observed spectral profile 604 may each represent a relative, as opposed to an absolute, distribution of spectral levels over the plurality of analysis channels 208. The reference spectral profile 602 and the observed spectral profile 604 may therefore be relative spectral profiles. A relative spectral profile determined from a particular incoming audio source may be the same, regardless of the absolute level of the incoming audio signal. For example, a relative spectral profile of a particular speaker may be the same, regardless of how loud the speaker is.

Hence, differences between the reference spectral profile 602 and the observed spectral profile 604 may represent differences in the relative distribution of spectral levels within the spectral profiles over the analysis channels 208 (i.e., the shapes of the profiles), as opposed to representing differences between the overall spectral levels at each of the analysis channels 208. The adjusted spectral profile 610 may then be determined by comparing the reference spectral profile 602 and the observed spectral profile 604, as described above. The adjusted spectral profile 610 may not be determined in situations where the reference spectral profile 602 and the observed spectral profile 604 do not differ, including in situations where the spectral profiles are relative spectral profiles.

Figure 7:
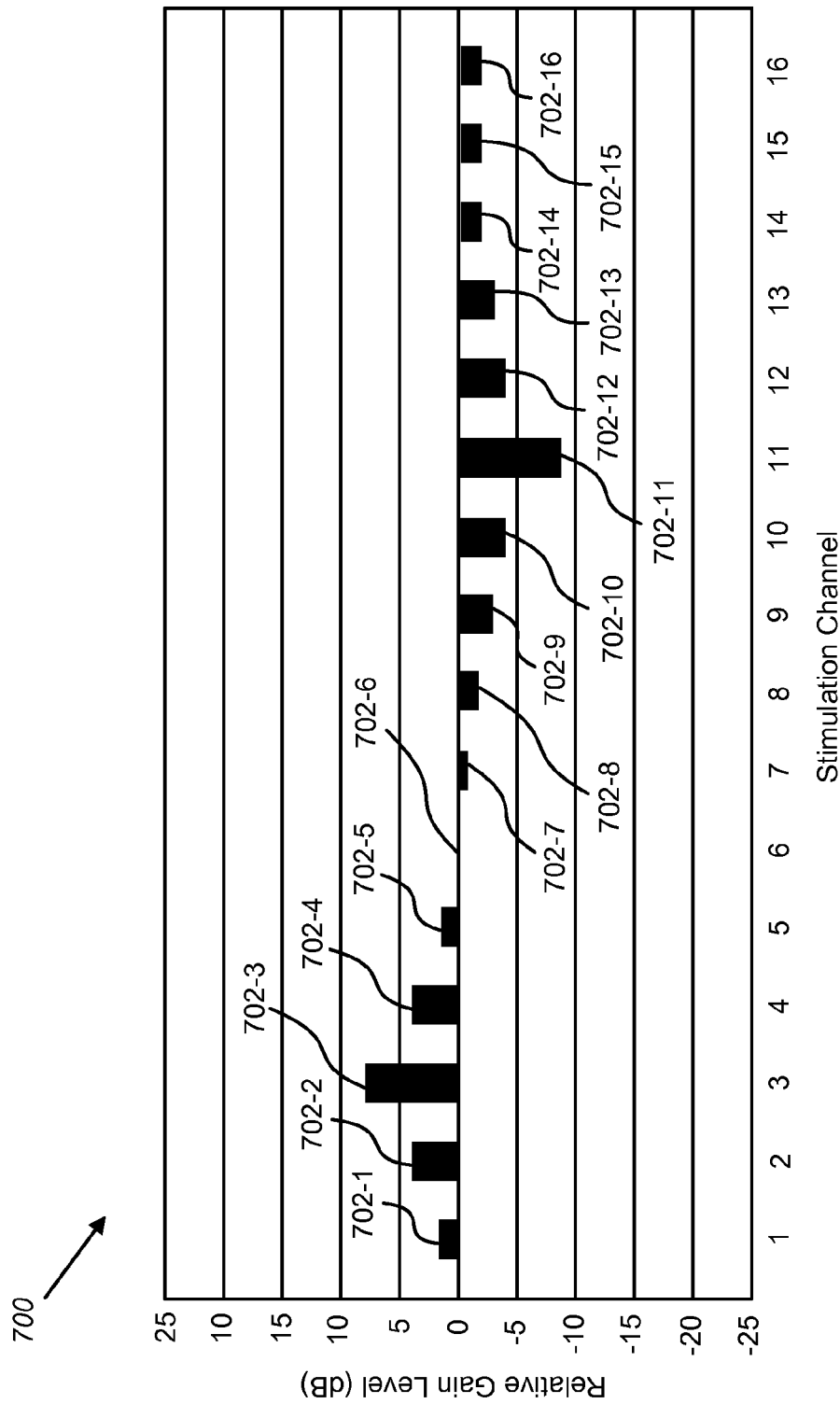
FIG. 7 depicts a graph showing exemplary gain parameter adjustments across a spectrum of stimulation channels according to principles described herein.

In some examples, sound processor 110 may be configured to direct the implantable cochlear stimulator 114 to apply electrical stimulation to a cochlear implant patient in accordance with the adjusted spectral profile 610 by adjusting one or more gain parameters corresponding to one or more stimulation channels 218. FIG. 7 depicts a graph 700 showing exemplary gain adjustments across a plurality of stimulation channels 218 according to principles described herein. As described above, the sound processor 110 may determine at least one adjusted spectral profile 610 that more closely matches the reference spectral profile 602 than does the observed spectral profile 604. The sound processor 110 may then adjust one or more gain parameters 702-1 through 702-16 (collectively referred to herein as "gain parameters 702") in accordance with the adjusted spectral profile 610. Each of the gain parameters 702 may correspond to a particular stimulation channel 218. One or more of the gain parameters 702 may be adjusted such that the electrical stimulation applied via the corresponding stimulation channels 218 is adjusted in accordance with the adjusted spectral profile 610.

To illustrate, gain parameters 702-1 through 702-5 may be adjusted such that the relative gain levels of channels 1 through 5 increase to match the gain levels of an adjusted spectral profile 610 that is identical to the reference spectral profile 602 shown in FIGS. 6A-6B. Likewise, gain parameters 702-7 through 702-16 may be adjusted such that the relative gain levels of channels 7 through 16 decrease to match the gain levels of an adjusted spectral profile 610 that is identical to the reference spectral profile 602 shown in FIGS. 6A-6B. It will be recognized that the gain parameters 702 may be alternatively adjusted in any other manner as may serve a particular application. In some examples, the gain parameters 702 may be adjusted in a manner such that the overall stimulation output level across all stimulation channels 218 applied to a patient may remain relatively constant. In other examples, gain parameters 702 may not be adjusted, such as in situations where the observed spectral profile 604 does not differ from the reference spectral profile 602.

Adjustment of one or more of the gain parameters 702 in accordance with the adjusted spectral profile 610, as illustrated in FIG. 7, may provide at least partial normalization or equalization of an incoming audio signal from the perspective of the cochlear implant patient. Such normalization may increase the ability of the patient to recognize speech or other contents of the audio signal.

Figure 8:
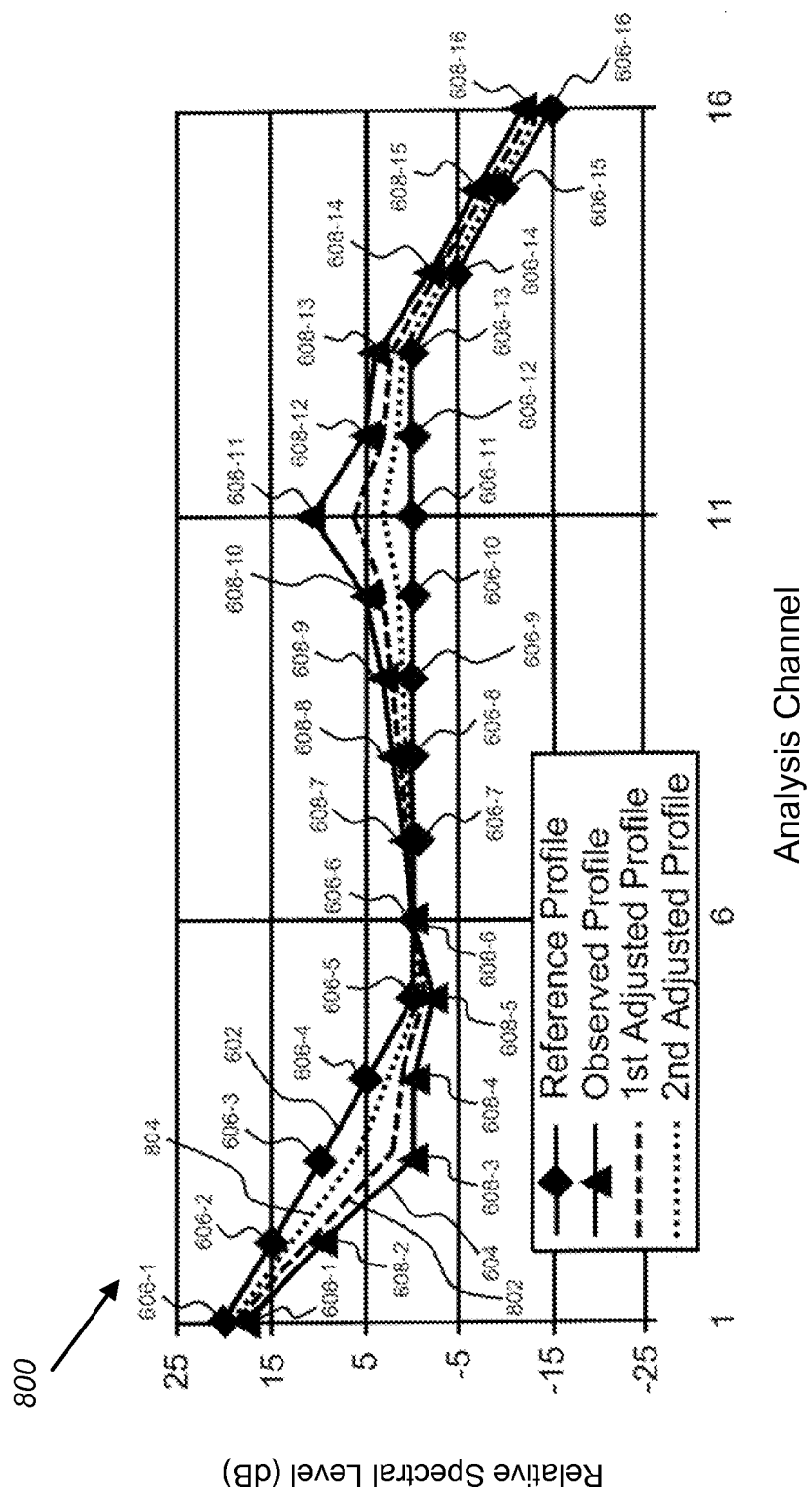
FIG. 8 depicts a graph showing exemplary spectral profiles across a spectrum of analysis channels according to principles described herein.

In some examples, the sound processor 110 may use a comparison between the reference spectral profile 602 and the observed spectral profile 604 to determine a plurality of adjusted spectral profiles, each of which may be closer to the reference spectral profile 602 than the observed spectral profile 604. Additionally, each of the plurality of adjusted spectral profiles may differ from one another. For example, FIG. 8 depicts a graph 800 including a first adjusted spectral profile 802 and a second adjusted spectral profile 804. As shown in FIG. 8, the first adjusted spectral profile 802 may differ from the second adjusted spectral profile 804. Additionally, the second adjusted spectral profile 804 may more closely match the reference spectral profile 602 than the first adjusted spectral profile 802.

Additionally or alternatively, one or more gain parameters 702 may be adjusted incrementally in accordance with a plurality of differing adjusted spectral profiles, such as the first adjusted spectra profile 802 and the second adjusted spectral profile 804. For example, one or more gain parameters 702 may be progressively adjusted such that the electrical stimulation applied to a cochlear implant patient is progressively adjusted in accordance with the plurality of adjusted spectral profiles, each of which may progressively more closely match the reference spectral profile. Accordingly, the electrical stimulation applied to a patient may be progressively and/or incrementally adjusted over a period of time, providing a relatively gradual adjustment of electrical stimulation applied to the patient. Adjusting the electrical stimulation applied to the patient in a relatively gradual manner, as opposed to suddenly changing the electrical stimulation, may enable the patient to more clearly perceive desired portions of an audio signal, such as a speech portion of the audio signal.

Hence, the systems and methods described herein facilitate adjustment and/or equalization of the spectral profile of incoming audio signals, thereby enabling a patient to hear and distinguish various portions of the incoming audio signals in various listening environments, including listening environments having relatively high levels of extraneous noise and/or in which speech portions of an audio signal are altered by the environment.

Figure 9:
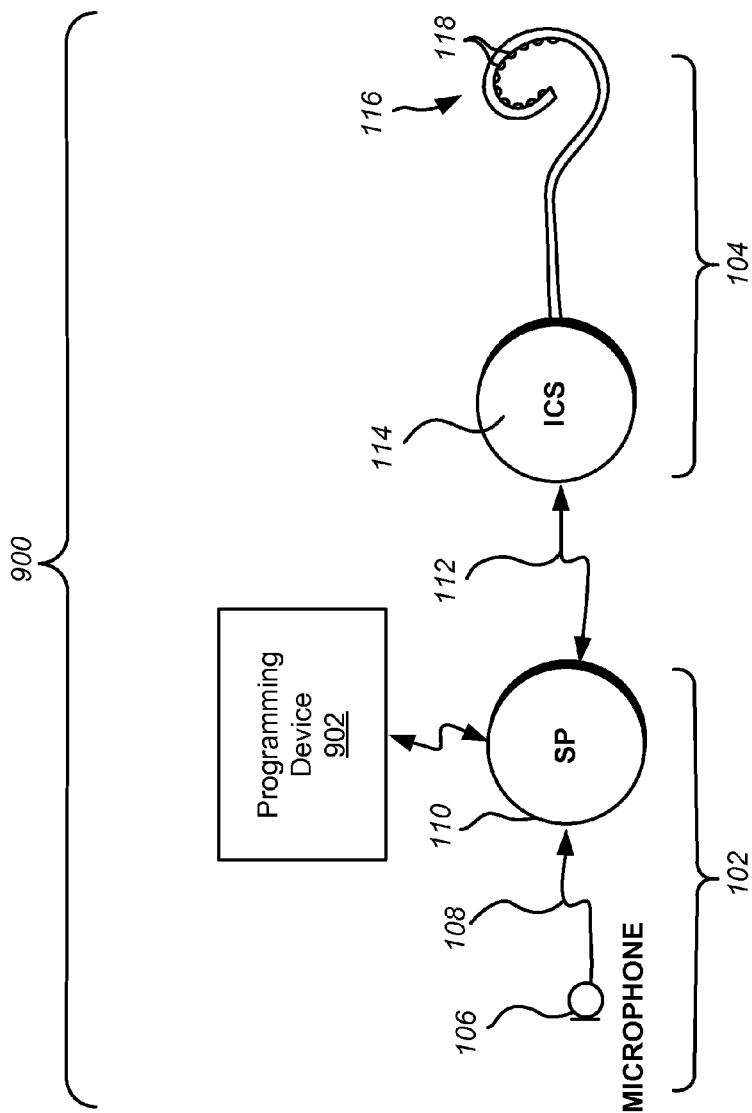
FIG. 9 illustrates an exemplary system configured to facilitate adjustment of a spectral profile of an incoming audio signal for a cochlear implant patient based at least in part on the listening environment of the patient according to principles described herein.

In some examples, the sound processor 110 may be configured to automatically adjust one or more gain parameters 702 to direct the implantable cochlear stimulator 114 to apply electrical stimulation to a cochlear implant patient in accordance with an adjusted spectral profile 610. In some alternative embodiments, the patient and/or another user may manually adjust one or more gain parameters 702. FIG. 9 illustrates an exemplary cochlear implant system 900 configured to facilitate manual adjustment of one or more gain parameters 702 by a user.

As shown in FIG. 9, a programming device 902 may be selectively and communicatively coupled to the sound processor 110. The programming device 902 may include any combination of hardware, software, and firmware configured to perform any of the functions described herein. For example, the programming device 902 may include a fitting station, personal computer, handheld device (e.g., a personal digital assistant), a mobile device (e.g., a mobile telephone), and/or any other electronic device as may serve a particular application. As will be described in more detail below, the programming device 902 may be configured to direct the implantable cochlear stimulator 114 to apply electrical stimulation representative of an audio signal to a cochlear implant patient in accordance with one or more adjusted spectral profiles 610 corresponding to an incoming audio signal.

Figure 10:
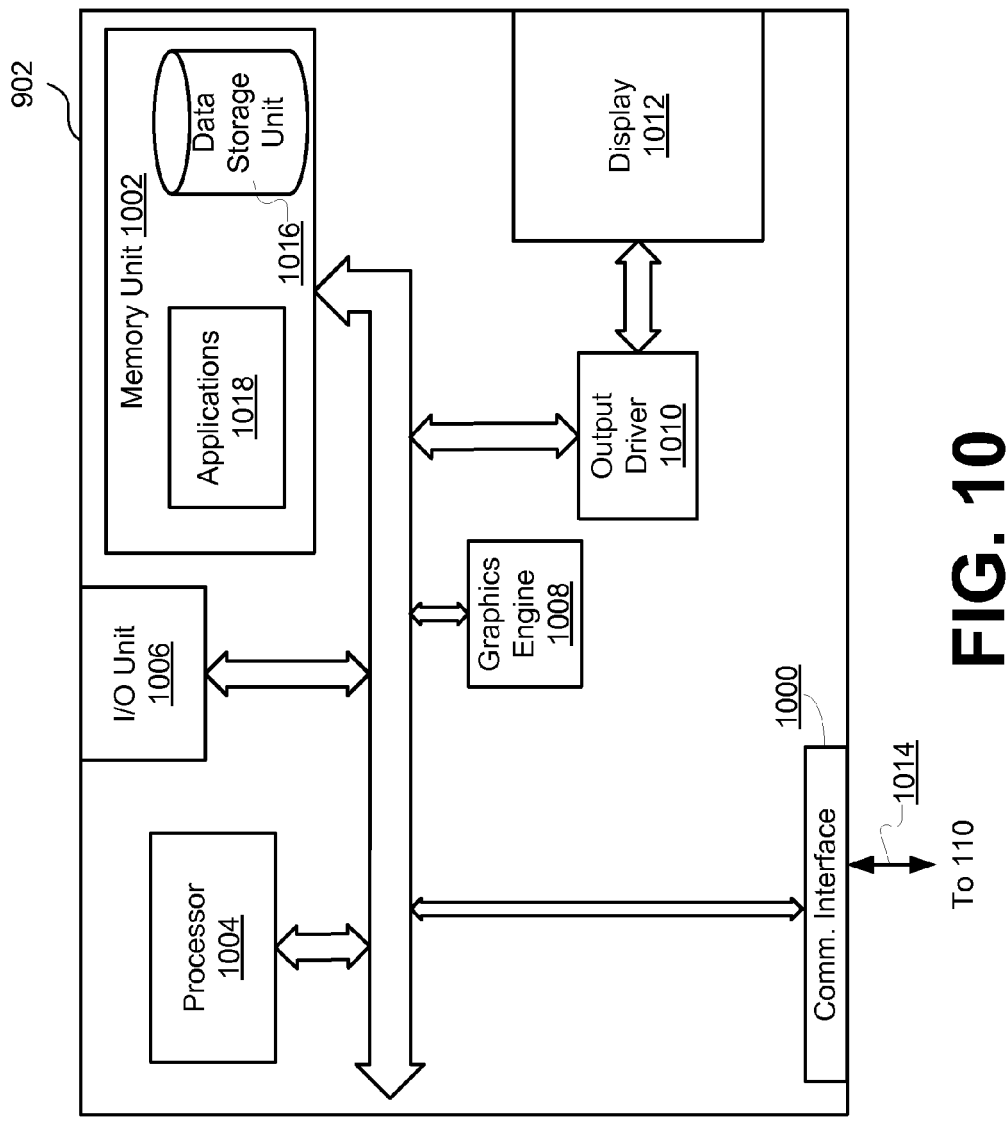
FIG. 10 illustrates a number of components that may be included within an exemplary programming device according to principles described herein.

FIG. 10 illustrates a number of components that may be included within an exemplary programming device 902. While an exemplary programming device 902 is shown in FIG. 10, the exemplary components illustrated in FIG. 10 are not intended to be limiting. Indeed, additional or alternative components and/or implementations may be included within the programming device 902.

In general, the programming device 902 may include any device configured to be selectively and communicatively coupled to one or more components of the cochlear implant system 100. For example, the programming device 902 may be selectively and communicatively coupled to the sound processor 110. Programming device 902 may also be configured to interact with various peripherals such as a terminal, keyboard, mouse, display screen, printer, stylus, input device(s), output device(s), and/or any other apparatus(es).

As shown in FIG. 10, the programming device 902 may include a communication interface 1000, programmable memory unit 1002, processor 1004, input/output unit 1006 ("I/O unit 1006"), graphics engine 1008, output driver 1010, and display 1012 communicatively connected to one another.

Communication interface 1000 may be configured to transmit and receive data to and from the sound processor 110. Exemplary data transmitted from the programming device 902 to the sound processor 110 includes programming data such as stimulation parameters (e.g., gain parameters) and the like. Exemplary data received by the programming device 902 from the sound processor 110 includes status data representative of a status of one or more components of the sound processor 110 and/or the implantable cochlear stimulator 114.

In some examples, a communications link 1014 may be used to facilitate communication between the programming device 902 and the sound processor 110. The communications link 1014 may include any type of link used to transmit data, such as, but not limited to, an RF link, an infrared (IR) link, an optical link, a Bluetooth link, a thermal link, a wire link, or any other suitable link.

Programmable memory unit 1002 may include, but is not limited to, FLASH memory, RAM, DRAM, or a combination thereof. The programmable memory unit 1002 may additionally or alternatively include a data storage unit 1016. The data storage unit 1016 may include one or more data storage media, devices, or configurations and may employ any type, form, and combination of storage media. For example, the data storage unit 1016 may include, but is not limited to, a hard drive, flash drive, optical disk, or other non-volatile storage unit. Data representative of one or more gain parameters and/or any other data may be stored within the data storage unit 616.

Processor 1004 may be configured to control one or more operations of the components included within the programming device 902. Processor 1004 may direct execution of operations in accordance with computer-executable instructions such as may be stored in memory unit 1002.

I/O unit 1006 may be configured to receive user input and provide user output and may include any hardware, firmware, software, or combination thereof supportive of input and output capabilities.

As instructed by processor 1004, graphics engine 1008 may generate graphics, which may include graphical user interfaces ("GUIs"). The output driver 1010 may provide output signals representative of the graphics generated by graphics engine 1008 to display 1012. The display 1012 may then present the graphics to the user.

One or more applications 1018 may be executed by the programming device 902. The applications, or application clients, may reside in memory unit 1002 or in any other area of the programming device 902 and be executed by the processor 1004. Each application 1018 may correspond to a particular feature or capability of the programming device 902. For example, illustrative applications 1018 may include one or more of a GUI application, data processing application, and/or stimulation parameter generation application.

It will be recognized that one or more processes and/or applications described herein may be implemented at least in part as computer-executable instructions, i.e., instructions executable by one or more computing devices, tangibly embodied in a computer-readable medium. In general, a processor (e.g., a microprocessor) receives instructions, e.g., from a memory, a computer-readable medium, etc., and executes those instructions, thereby performing one or more processes, including one or more of the processes described herein. Such instructions may be stored and transmitted using a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media, volatile media, and transmission media. Non-volatile media may include, for example, optical or magnetic disks and other persistent memory. Volatile media may include, for example, DRAM, which typically constitutes a main memory. Transmission media may include, for example, coaxial cables, copper wire and fiber optics, including the wires that comprise a system bus coupled to a processor of a computer. Transmission media may include or convey acoustic waves, light waves, and electromagnetic emissions, such as those generated during RF and infrared IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

As mentioned, the programming device 902 may be configured to adjust one or more gain parameters corresponding to one or more of the stimulation channels 218. Additionally or alternatively, the programming device 902 may be configured to direct the sound processor 110 to adjust one or more gain parameters corresponding to one or more of the stimulation channels 218. Accordingly, the programming device 902 may enable a user to adjust stimulation representative of an incoming audio signal applied to a patient in accordance with an adjusted spectral profile 610 determined by the user, the programming device 902, and/or the sound processor 110.

Figure 11:
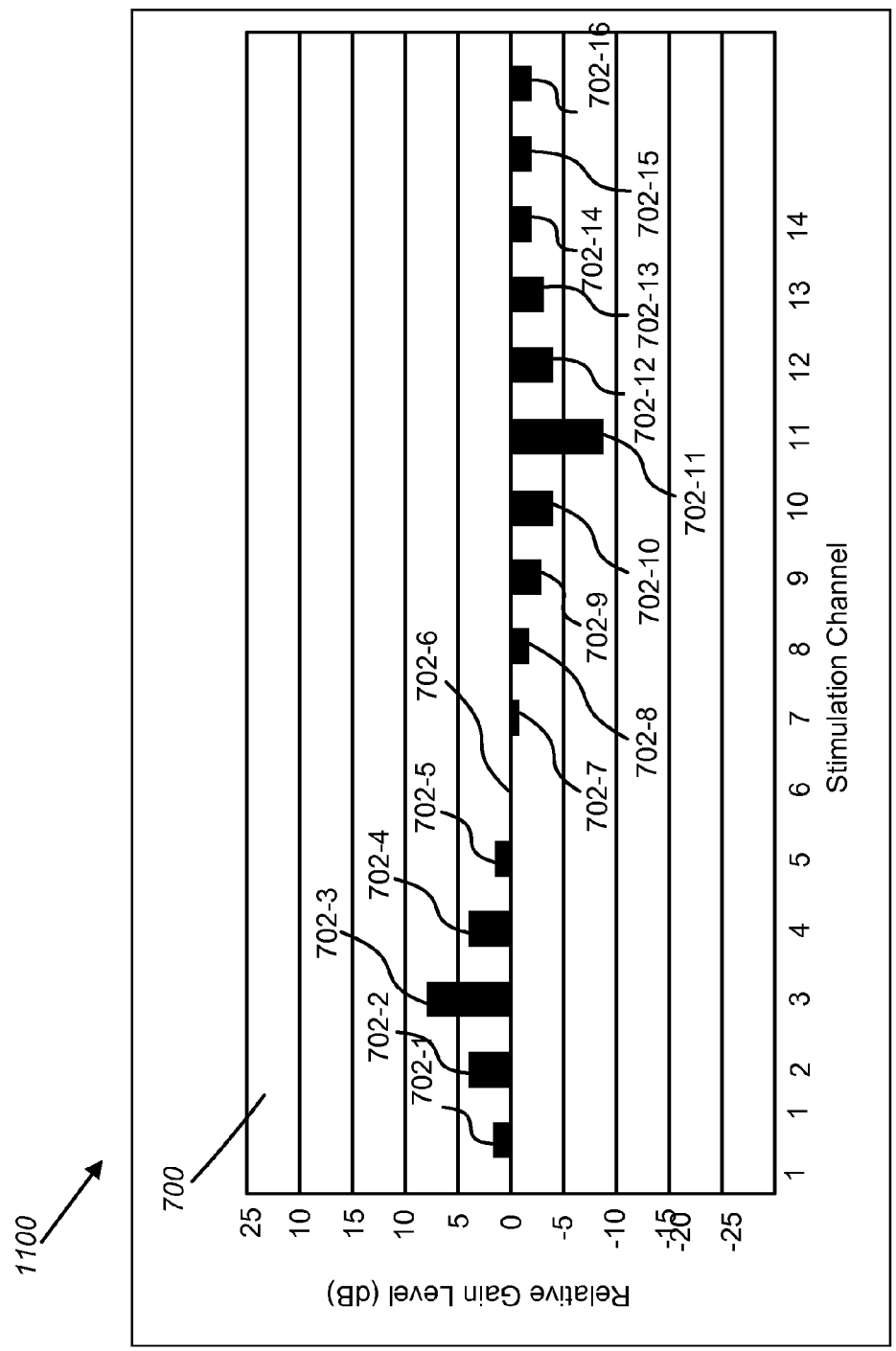
FIG. 11 shows a graphical user interface that may be displayed by a programming device and that is configured to facilitate adjustment of one or more gain parameters across a spectrum of stimulation channels according to principles described herein.

In some examples, the programming device 902 may be configured to generate and display a GUI configured to facilitate adjustment of one or more gain parameters 702. For example, FIG. 11 shows a GUI 1100 that may be displayed by programming device 902 and that is configured to facilitate adjustment of one or more gain parameters 702 for a particular cochlear implant patient. As shown in FIG. 11, GUI 1100 may include a depiction of graph 700 so that a clinician or other user thereof may visually see the gain parameters 702 over a range of stimulation channels 218.

A user may adjust one or more gain parameters 702 shown in GUI 1100 in any suitable manner. For example, a clinician or other user may select a graphic representing particular gain parameter 702 corresponding to a particular stimulation channel, such as gain parameter 702-1. The user may then adjust the selected gain parameter 702-1 by adjusting a size of the selected graphic. In some examples, a user may use a mouse pointer or arrow key on a keyboard to drag or otherwise move the selected gain parameter 702-1 up or down, thereby increasing or decreasing the relative gain level of the selected gain parameter 702-1. Alternatively, a user may manually type in a desired relative gain level for the selected gain parameter 702-1.

Figure 12:
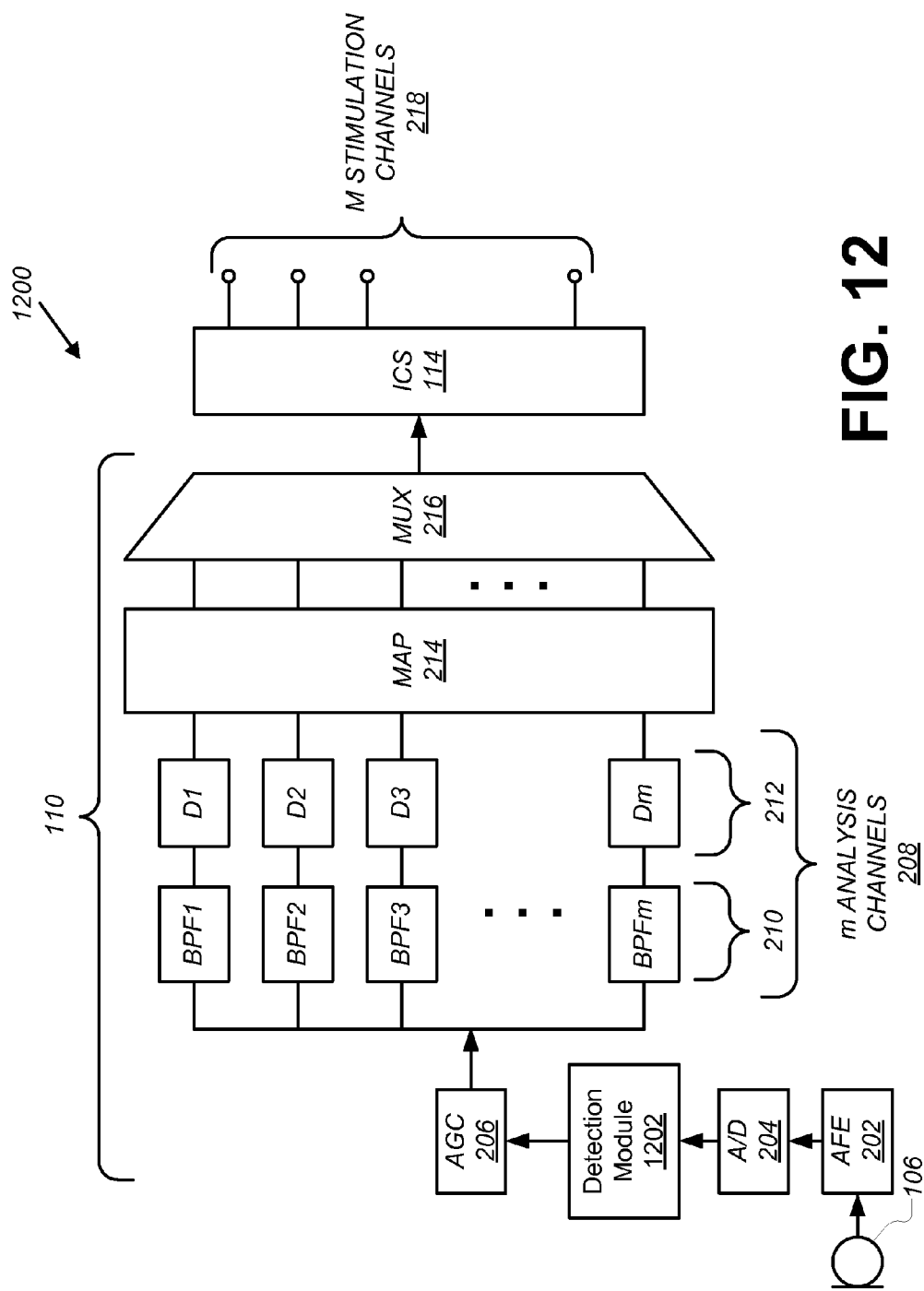
FIG. 12 illustrates a functional block diagram of an exemplary cochlear implant system configured to detect a spectral profile of an incoming audio signal and apply electrical stimulation representative of the incoming audio signal to a patient according to principles described herein.

FIG. 12 illustrates a functional block diagram of an exemplary cochlear implant system 1200 configured to measure sound levels of incoming audio signals in various listening environments and configured to detect a listening environment of a patient and generate an adjusted spectral profile accordingly. As shown in FIG. 12, the sound processor 110 may include a detection module 1202 configured to detect a listening environment of the patient. The detection module 1202 may detect the listening environment of a patient using any process or heuristic as may serve a particular application.

The sound processor 110 may generate an adjusted spectral profile in accordance with the detected listening environment. For example, the sound processor 110 may be configured to generate an adjusted spectral profile that compensates for a listening environment having a particularly high amount of noise.

Figure 13:
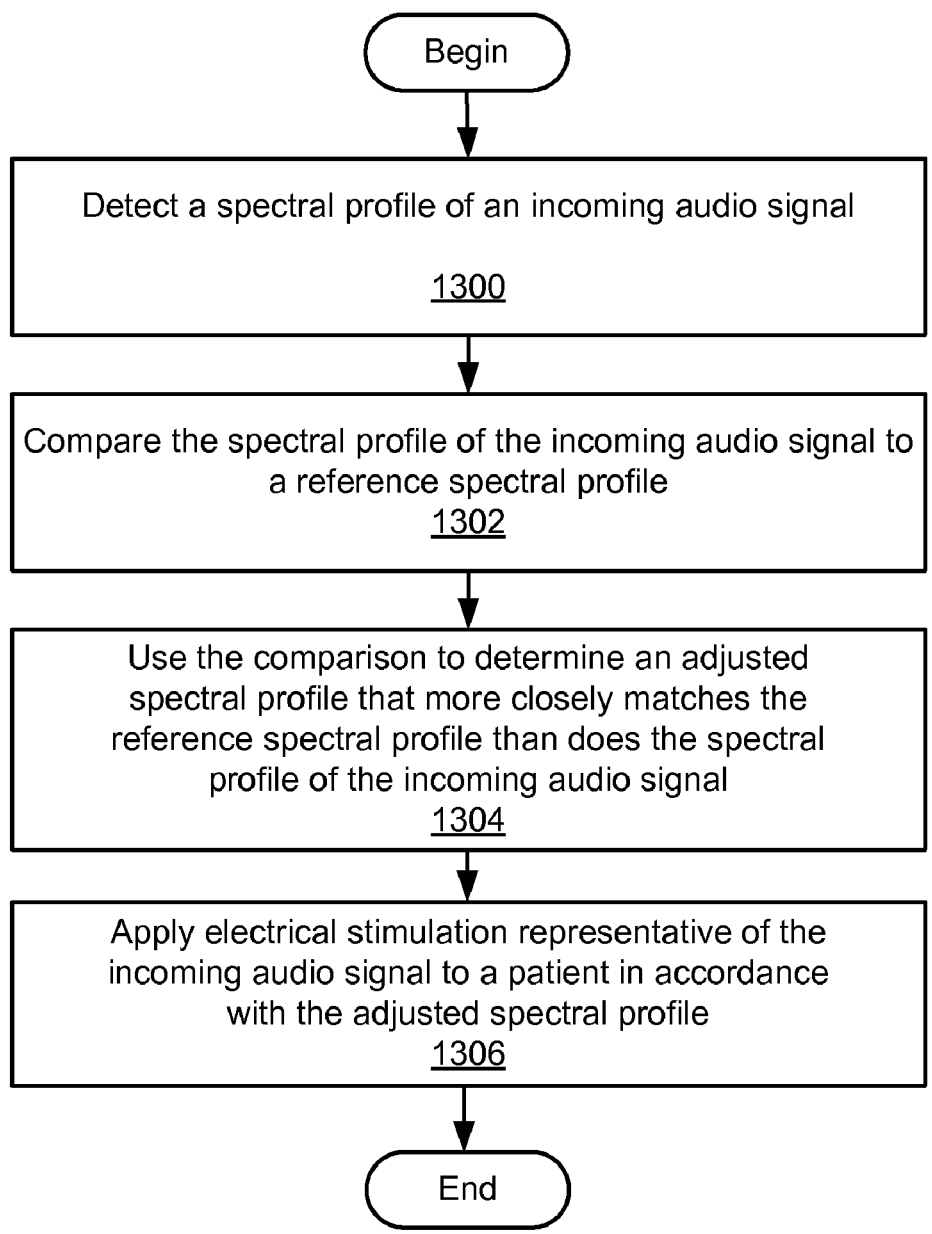
FIG. 13 illustrates an exemplary method of adjusting a spectral profile of an incoming audio signal for a cochlear implant patient according to principals described herein.

FIG. 13 illustrates an exemplary method of adjusting a spectral profile corresponding to an incoming audio signal for a cochlear implant patient. While FIG. 13 illustrates exemplary steps according to one embodiment, other embodiments may omit, add to, reorder, and/or modify any of the steps shown in FIG. 13.

In step 1300, a spectral profile of an incoming audio signal is detected. The spectral profile may be detected in any of the ways described herein.

In step 1302, the spectral profile of the incoming audio signal is compared to a reference spectral profile. The reference spectral profile may represent an average spectral profile of one or more audio signals, a pre-determined spectral profile, or any other spectral profile as may serve a particular application. The comparison of the spectral profiles may be performed in any of the ways described herein.

In step 1304, the comparison is used to determine an adjusted spectral profile that more closely matches the reference spectral profile than does the spectral profile of the incoming audio signal. The adjusted spectral profile may be determined and generated in any of the ways described herein.

In step 1306, electrical stimulation representative of the incoming audio signal is applied to a patient in accordance with the adjusted spectral profile. One or more gain parameters corresponding to one or more stimulation channels may be adjusted to apply electrical stimulation to the patient in accordance with the adjusted spectral profile as described herein.

Figure 14:
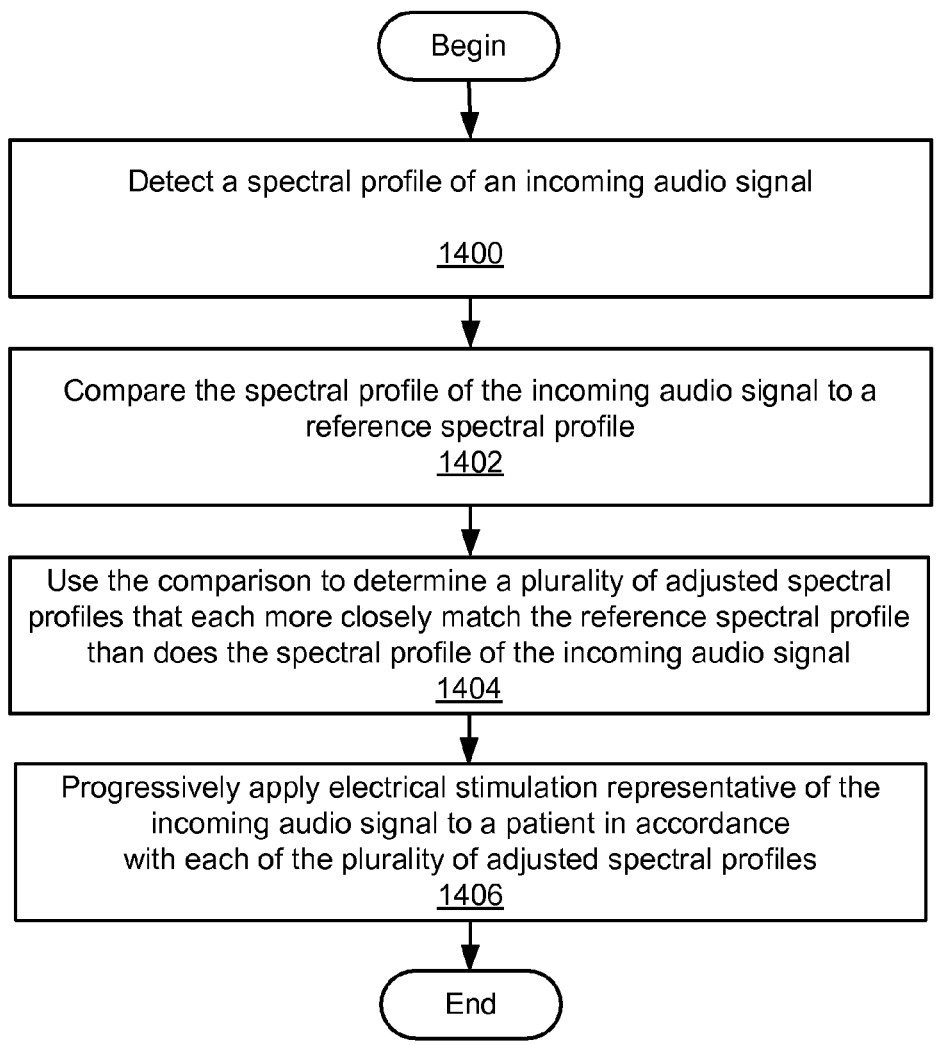
FIG. 14 illustrates another exemplary method of adjusting a spectral profile of an incoming audio signal for a cochlear implant patient according to principals described herein.

FIG. 14 illustrates an additional exemplary method of adjusting a spectral profile corresponding to an incoming audio signal for a cochlear implant patient. While FIG. 14 illustrates exemplary steps according to one embodiment, other embodiments may omit, add to, reorder, and/or modify any of the steps shown in FIG. 14.

In step 1400, a spectral profile of an incoming audio signal is detected. The spectral profile may be detected in any of the ways described herein.

In step 1402, the spectral profile of the incoming audio signal is compared to a reference spectral profile. The comparison of the spectral profiles may be performed in any of the ways described herein.

In step 1404, the comparison is used to determine a plurality of adjusted spectral profiles that each more closely matches the reference spectral profile than does the spectral profile of the incoming audio signal. The plurality of adjusted spectral profiles may be determined and generated in any of the ways described herein.

In step 1406, electrical stimulation representative of the incoming audio signal is progressively applied to a patient in accordance with each of the adjusted spectral profiles. One or more gain parameters corresponding to one or more stimulation channels may be adjusted to apply electrical stimulation to the patient in accordance with the plurality of adjusted spectral profiles as described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   detecting a plurality of incoming audio signals presented to a cochlear implant patient;
   determining a plurality of spectral profiles corresponding to the plurality of incoming audio signals;
   determining a reference spectral profile for said cochlear implant patient based on the determined plurality of spectral profiles;
   detecting an incoming audio signal presented to the cochlear implant patient after the plurality of incoming audio signals are presented to the cochlear implant patient;
   determining a spectral profile of the incoming audio signal;
   comparing said spectral profile of said incoming audio signal to said reference spectral profile;
   using said comparison to determine an adjusted spectral profile that more closely matches said reference spectral profile than does said spectral profile of said incoming audio signal; and
   applying electrical stimulation representative of said incoming audio signal to said patient in accordance with said adjusted spectral profile.

2. The method of claim 1, further comprising:
   detecting a spectral profile of another incoming audio signal;
   comparing said spectral profile of said another incoming audio signal to said reference spectral profile;
   using said comparison of said spectral profile of said another incoming audio signal to said reference spectral profile to determine another adjusted spectral profile that more closely matches said reference spectral profile than does said adjusted spectral profile; and
   applying electrical stimulation representative of said another incoming audio signal to a patient in accordance with said another adjusted spectral profile.

3. The method of claim 1, wherein said comparing said spectral profile of said incoming audio signal to said reference spectral profile comprises determining a difference between a spectral level of said incoming audio signal and a spectral level of said reference spectral profile within each of one or more analysis channels.

4. The method of claim 3, further comprising adjusting one or more gain parameters each corresponding to a stimulation channel associated with one of said analysis channels such that said adjusted spectral profile more closely matches said reference spectral profile, said gain parameters configured to at least partially define said electrical stimulation applied to said patient.

5. The method of claim 4, further comprising automatically adjusting one or more of said gain parameters.

6. The method of claim 4, further comprising facilitating manual adjustment of one or more of said gain parameters.

7. The method of claim 1, wherein said incoming audio signal comprises speech.

8. The method of claim 1, wherein said determining of the reference spectral profile comprises determining an average of the determined plurality of spectral profiles.

9. The method of claim 8, wherein said plurality of incoming audio signals are presented to said cochlear implant patient over a period of at least 10 seconds prior to said presentation of said incoming audio signal to said cochlear implant patient.

10. The method of claim 8, further comprising updating said average spectral profile with said spectral profile of said incoming audio signal.

11. The method of claim 10, wherein said incoming audio signal further comprises noise, wherein said method further comprises at least partially removing said noise from said incoming audio signal prior to updating said average spectral profile with said spectral profile of said incoming audio signal.

12. The method of claim 8, further comprising updating said average spectral profile with said spectral profile of said incoming audio signal only if a signal-to-noise ratio of said incoming audio signal is above a predefined threshold.

13. The method of claim 1, wherein said adjusted spectral profile substantially matches said reference spectral profile.

14. A method comprising:
   detecting a plurality of incoming audio signals presented to a cochlear implant patient;
   determining a plurality of spectral profiles corresponding to the plurality of incoming audio signals;

determining a reference spectral profile for said cochlear implant patient based on the determined plurality of spectral profiles;

detecting an incoming audio signal presented to the cochlear implant patient after the plurality of incoming audio signals are presented to the cochlear implant patient;

determining a spectral profile of the incoming audio signal;

comparing said spectral profile of said incoming audio signal to said reference spectral profile;

using said comparison to determine a plurality of adjusted spectral profiles that each more closely match said reference spectral profile than does said spectral profile of said incoming audio signal; and progressively applying electrical stimulation representative of said incoming audio signal to said patient in accordance with each of said plurality of adjusted spectral profiles.

15. The method of claim 14, wherein said applying electrical stimulation to said patient comprises progressively adjusting said electrical stimulation in accordance with individual adjusted spectral profiles from said plurality of adjusted spectral profiles such that each of said individual adjusted spectral profiles progressively more closely matches said reference spectral profile.

16. The method of claim 14, wherein said applying electrical stimulation to said patient comprises incrementally varying said electrical stimulation in accordance with each of said plurality of adjusted spectral profiles.

17. The method of claim 14, wherein said comparing said spectral profile of said incoming audio signal to said reference spectral profile comprises determining a difference between a spectral level of said incoming audio signal and a spectral level of said reference spectral profile within each of one or more analysis channels.

18. A method of comprising:
  detecting a plurality of incoming audio signals presented to a cochlear implant patient;
  determining a plurality of spectral profiles corresponding to the plurality of incoming audio signals;
  determining a reference spectral profile for said cochlear implant patient based on the determined plurality of spectral profiles;
  detecting an incoming audio signal presented to the cochlear implant patient after the plurality of incoming audio signals are presented to the cochlear implant patient;
  identifying a portion of said incoming audio signal that does not contain a noise component;
  updating said reference spectral profile based on the portion of said incoming audio signal that does not include said noise component;
  detecting a spectral profile of said incoming audio signal;
  comparing said spectral profile of said incoming audio signal to said reference spectral profile that has been updated based on the portion of the incoming audio signal that does not include said noise component;
  using said comparison to determine an adjusted spectral profile that more closely matches said reference spectral profile than does said spectral profile of said incoming audio signal; and
  applying electrical stimulation representative of said incoming audio signal to a patient in accordance with said adjusted spectral profile.

19. A cochlear implant system, comprising:
  a sound processor configured to
    detect a plurality of incoming audio signals presented to a cochlear implant patient,
    determine a plurality of spectral profiles corresponding to the plurality of incoming audio signals,
    determine a reference spectral profile for said cochlear implant patient based on the determined plurality of spectral profiles,
    detect an incoming audio signal presented to the cochlear implant patient after the plurality of incoming audio signals are presented to the cochlear implant patient
    determining a spectral profile of the incoming audio signal,
    compare said spectral profile of said incoming audio signal to said reference spectral profile,
    use said comparison to determine an adjusted spectral profile that more closely matches said reference spectral profile than does said spectral profile of said incoming audio signal; and
  an implantable cochlear stimulator communicatively coupled to said sound processor and configured to apply electrical stimulation representative of said incoming audio signal to a patient in accordance with said adjusted spectral profile.

20. The system of claim 19, wherein said sound processor is configured to detect a spectral profile of another incoming audio signal and compare said spectral profile of said another incoming audio signal to said reference spectral profile, wherein said sound processor is further configured to use said comparison of said spectral profile of said another incoming audio signal to said reference spectral profile to determine another adjusted spectral profile that more closely matches said reference spectral profile than does said adjusted spectral profile; and
  wherein said implantable cochlear stimulator is further configured to apply electrical stimulation representative of said another incoming audio to a patient in accordance with said another adjusted spectral profile.

21. The system of claim 19, wherein said sound processor is further configured to determine a difference between a spectral level of said incoming audio signal and a spectral level of said reference spectral profile within each of one or more analysis channels.

* * * * *